United States Patent [19]
Hansenne

[11] Patent Number: 5,955,091
[45] Date of Patent: Sep. 21, 1999

[54] PHOTOBLUING/WHITENING-RESISTANT COSMETIC/DERMATOLOGICAL COMPOSITIONS COMPRISING TIO₂ PIGMENTS AND DEFORMABLE HOLLOW PARTICULATES

[75] Inventor: Isabelle Hansenne, Paris, France

[73] Assignee: Société l'Oréal S.A., Paris, France

[21] Appl. No.: 08/679,806

[22] Filed: Jul. 15, 1996

[30] Foreign Application Priority Data

Jul. 13, 1995 [FR] France ................................. 95 08564
Jul. 13, 1995 [FR] France ................................. 95 08565

[51] Int. Cl.⁶ .................................................. A61K 7/48
[52] U.S. Cl. ............................................ 424/401; 424/59
[58] Field of Search ..................... 424/401, 59; 514/844, 514/845, 846, 937

[56] References Cited

U.S. PATENT DOCUMENTS

| | | | |
|---|---|---|---|
| 5,314,683 | 5/1994 | Schlossman | 424/63 |
| 5,593,680 | 1/1997 | Bara et al. | 424/401 |
| 5,616,331 | 4/1997 | Allard et al. | 424/401 |
| 5,695,747 | 12/1997 | Forestier et al. | 424/59 |

FOREIGN PATENT DOCUMENTS

| | | |
|---|---|---|
| 2700952 | 8/1994 | France . |
| 2521003 | 5/1994 | Germany . |
| 2191945 | 12/1987 | United Kingdom . |

OTHER PUBLICATIONS

Chemical Abstracts, vol. 104, No. 4, Jan. 27, 1986, Columbus, Ohio, USA, Abstract No. 24076w, p. 290, & JP–A–60 184 004 (Pola Chemical Industries Inc.), Sep. 19, 1985.

Patent Abstracts of Japan, vol. 11, No. 18 (C–398) [2465], Jan. 17, 1987 & JP–A 61 194 013 (Taisho Pharmaceut. Co. Ltd.), Aug. 28, 1986.

*Primary Examiner*—Jyothsna Venkat
*Attorney, Agent, or Firm*—Burns, Doane, Swecker & Mathis, L.L.P.

[57] ABSTRACT

Topically applicable cosmetic/sunscreen/dermatological compositions, well suited for improved photoprotection of human skin and/or hair against the damaging effects of UV-A and UV-B irradiation and/or for the therapeutic treatment of a disease state of the skin or mucosae, essentially in the absence of photobluing/whitening, comprise at least one titanium dioxide (nano)pigment and an effective photobluing/whitening-reducing amount of deformable hollow particulates (microspheres) having a particle size ranging from 1 $\mu$m to 250 $\mu$m and which comprise an expanded copolymer of vinylidene chloride, acrylonitrile and a (meth) acrylate.

16 Claims, No Drawings

PHOTOBLUING/WHITENING-RESISTANT COSMETIC/DERMATOLOGICAL COMPOSITIONS COMPRISING TIO₂ PIGMENTS AND DEFORMABLE HOLLOW PARTICULATES

CROSS-REFERENCE TO COMPANION APPLICATION

Copending application Serial No. 08/678,416 [Attorney Docket No. 016800-099], filed concurrently herewith and assigned to the assignee hereof.

BACKGROUND OF THE INVENTION

1. Technical Field of the Invention

The present invention relates to the formulation of particular deformable hollow particles into cosmetic and/or dermatological compositions containing titanium dioxide (nano)pigments, to reduce the photobluing initiated by the presence of said pigments and/or the whitening usually occurring when this type of composition is topically applied onto human skin. Such hollow particles exhibit a particle size ranging from 1 $\mu$m to 250 $\mu$m and comprise an expanded copolymer of vinylidene chloride, a (meth)acrylate and acrylonitrile.

The compositions according to the invention may, in particular, be topically applied for protecting the skin and hair against light, in the form of sunscreen compositions, as well as for makeup, care and hygiene of the skin, of the face, of the human body including the scalp and the mucosae, the hair and, lastly, for the therapeutic treatment of the skin and of the mucosae. Thus, the compositions of the invention may comprise an oil-in-water emulsion, a water-in-oil emulsion, a care cream or lotion, a balm, a blusher, a fluid or cast foundation, or a dermopharmaceutical ointment.

2. Description of the Prior Art

It is known to this art that light radiation of wavelengths of from 280 nm to 400 nm promote tanning of the human epidermis and that irradiation with wavelengths between 280 nm and 320 nm, i.e., UV-B irradiation, causes erythemas and skin burns which impair the development of the natural tan; hence, this UV-B radiation must thus be screened or blocked from the skin.

It is also known to this art that UV-A radiation, of wavelengths of from 320 nm to 400 nm, which tans the skin, also adversely affects it, especially in the case of sensitive skin or skin which is constantly exposed to solar radiation. In particular, UV-A irradiation causes a loss in skin elasticity and promotes the appearance of wrinkles, resulting in premature aging. Such irradiation promotes triggering of the erythematous reaction or amplifies this reaction in certain individuals, and may even be the source of phototoxic or photoallergic reactions. Thus, it is desirable to also screen out UV-A radiation.

A wide variety of sunscreens, inorganic pigments and organic screening agents, exist on the market for screening out UV-A and UV-B radiations. These sunscreens must be capable of absorbing or blocking the harmful rays of the sun, while at the same time remaining innocuous to the user.

Thus, many organic sunscreens capable of absorbing harmful UV irradiation more or less selectively are known to the cosmetics art. For a variety of reasons, however, these screening agents are not entirely satisfactory.

Accordingly, it is increasingly sought to avoid the use of these organic screening agents by favoring the use of inorganic pigments, which also act as sunscreens, principally by scattering/reflecting the UV, while contributing greater safety for the user.

In this respect, the inorganic pigment most widely employed to date is titanium dioxide, the screening or blocking properties of which are well known to this art.

In order to attain suitable protection factors, however, it is necessary to formulate high percentages of TiO₂, in particular higher than 5% by weight, into the sunscreen compositions.

However, with such amounts of TiO₂, compositions containing these pigments exhibit instability to light in an oxygen-free medium, which is manifested by the appearance of a blue coloration (photocoloring known as photobluing). Also, the appearance of whitening when these compositions are applied to the skin is observed. These two phenomena are obviously not desirable from an aesthetic standpoint.

SUMMARY OF THE INVENTION

It has now surprisingly and unexpectedly been determined that formulating deformable hollow particulates having a particular density and particle size into a composition containing TiO₂ pigments significantly reduces the photobluing and whitening phenomena intrinsically associated with such composition.

In addition to the reduction in the photobluing and whitening phenomena, the subject particulates also impart softness and homogeneity on application, as well as greater spreadability.

Briefly, the present invention features formulating deformable hollow particulates into cosmetic and/or dermatological compositions containing TiO₂ pigments, for reducing or eliminating the photobluing attributed to the presence of said pigments and/or the whitening when such compositions are applied to skin; the subject hollow particles have a particle size ranging from 1 $\mu$m to 250 $\mu$m and comprise an expanded copolymer of vinylidene chloride, acrylonitrile and methyl (meth)acrylate.

DETAILED DESCRIPTION OF BEST MODE AND SPECIFIC/PREFERRED EMBODIMENTS OF THE INVENTION

More particularly according to the present invention, by the term "deformable" is intended that the particles are flexible and resilient or elastic; after crushing they resume their initial shape.

The subject particulates generally have a particle size ranging from 1 $\mu$m to 250 $\mu$m.

The subject particulates advantageously have a particle size less than 100 $\mu$m. Indeed, the finer the particles, the "softer" the composition is when topically applied. The particles preferably have a particle size ranging from 10 $\mu$m to 60 $\mu$m.

The particles advantageously have a density ranging from 15 kg/m³ to 200 kg/m³ and, preferably, greater than 40 kg/m³ and/or lower than 100 kg/m³ and, more preferably, ranging from 60 kg/M³ to 80 kg/m³.

Exemplary copolymers comprise from 1% to 60% of recurring structural units derived from vinylidene chloride, from 20% to 90% of recurring structural units derived from acrylonitrile and from 1% to 50% of recurring structural units derived from an acrylic monomer, the sum of the percentages (by weight) being equal to 100. The acrylic monomer may be, for example, a methyl acrylate or methacrylate and, in particular, the methacrylate. These particles are especially in the dry or hydrated state.

This copolymer is nontoxic and non-irritating to the skin.

The particles, or beads, are preferably in the form of microspheres.

The particles of the invention may be prepared, for example, according to the processes described in EP-56,219, EP-348,372, EP-486,080, EP-320,473, EP-112,807 and U.S. Pat. No. 3,615,972.

The internal cavity of the subject particulates contains a gas which may be air, nitrogen or a hydrocarbon like isobutane or isopentane.

The hollow particles which are useful according to the invention include, in particular, those marketed under the trademark Expancel by Nobel Casco, such as Expancel 551 DE 20 of 30 μm particle size and having a density of approximately 65 kg/m$^3$, and Expancel 551 DE 50 of 40 μm particle size.

In the compositions of the invention, from 0.1% to 10% by weight of particles and, advantageously, from 0.3% to 5% by weight and, more advantageously, from 0.3% to 2% by weight, is preferably incorporated therein, relative to the total weight of the composition.

One of the essential characteristics of the compositions according to the present invention is the inclusion of titanium dioxide pigments. The pigments of this invention are known titanium dioxide pigments, typically employed in the field of cosmetics as fillers or sunscreens, which may either be treated or untreated. Such pigments include the titanium dioxide nanopigments. By the term "nanopigments" are intended pigments in which the average size of the elementary particles ranges from 5 to 100 nm.

The titanium dioxide may be in rutile, anatase or amorphous form, but is preferably in the rutile and/or anatase form.

The treated pigments may, for example, be surface treated with alumina, silica, aluminum compounds, silicon compounds, sodium compounds, iron oxides, iron esters, stearic acid or glycerin.

More particularly, exemplary treated pigments include:
(1) silica and alumina, such as the products "Microtitanium Dioxide MT 500 SA" and "Microtitanium Dioxide MT 100 SA" marketed by Tayca, and the products "Tioveil Fin", "Tioveil OP", "Tioveil MOTG" and "Tioveil IPM" marketed by Tioxide,
(2) alumina and aluminum stearate, such as the product "Microtitanium Dioxide MT 100 T" marketed by Tayca,
(3) alumina and aluminum laurate, such as the product "Microtitanium Dioxide MT 100 S" marketed by Tayca,
(4) iron oxides and iron stearate, such as the product "Microtitanium Dioxide MT 100 F" marketed by Tayca,
(5) silica, alumina and silicone, such as the products "Microtitanium Dioxide MT 100 SAS," "Microtitanium Dioxide MT 600 SAS" and "Microtitanium Dioxide MT 500 SAS" marketed by Tayca,
(6) sodium hexametaphosphate, such as the product "Microtitanium Dioxide MT 150 W" marketed by Tayca,
(7) octyltrimethoxysilane, such as the product "T-805" marketed by Degussa,
(8) alumina and stearic acid, such as the product "UVT-M160" marketed by Kemira,
(9) alumina and glycerin, such as the product "UVT-M212" marketed by Kemira, and
(10) alumina and silicone, such as the product "UVT-M262" marketed by Kemira.

The untreated titanium dioxides include for example, those marketed by Tayca under the trademark "Microtitanium Dioxide MT 500 B" and "Microtitanium Dioxide MT 600 B."

The titanium dioxide (nano)pigment(s) may be incorporated in the compositions according to the invention in a proportion ranging from 1% to 30% by weight relative to the total weight of the composition, preferably from 2% to 25% by weight relative to the total weight of the composition.

According to the present invention, relatively large amounts of TiO$_2$, can be incorporated without difficulty or disadvantage, in particular amounts greater than 5% by weight or, or even greater than 10% by weight, or, still further, greater than 15% by weight. Too, these high-TiO$_2$ compositions do not exhibit the photobluing drawback indicated above.

The other constituents that may be formulated into the compositions of the invention, in particular the oils, the waxy compounds, the thickeners, the emulsifiers and the gelling agents, are those that are conventionally employed in the cosmetics and/or dermatology arts.

By the term "oil" is intended a compound that is liquid at ambient temperature. By the term "wax" is intended a compound that is solid or substantially solid at ambient temperature and whose melting point is generally higher than 35° C.

Oils that are exemplary are the mineral oils (vaseline), plant and vegetable oils (sweet almond, macadamia, currant seed oil), synthetic oils such as perhydrosqualene; fatty alcohols, acids or esters (octyl palmitate, isopropyl lanolate and triglycerides including those of capric/caprylic acids); oxyethylenated or oxypropylenated fatty esters; and ethers; silicone oils (cyclomethicone, polydimethyl-siloxanes or PDMS) or fluorinated oils; and polyalkylenes.

Waxy compounds which are exemplary are jojoba oil, paraffin wax, carnauba wax, beeswax and hydrogenated castor oil.

Exemplary emulsifiers include the esters of fatty acids and polyethylene glycol (PEG), the esters of fatty acids and of glycerol (glyceryl stearate) or the esters of fatty acids and sugar (sorbitan stearate), as well as the polyoxyethylenated or polyoxypropylenated derivatives thereof, cyclomethicones and dimethicone copolyols, anionic surfactants (K or Na alkyl phosphate) and polyalkoxylated fatty alcohols. Polyalkoxylated fatty alcohols are preferably employed, such as oxypropylenated butyl alcohols, oxyethylenated caprylyl alcohols and oxyethylenated cetyl alcohols.

Thickeners which may be formulated include crosslinked polyacrylic acids, guar gums and optionally modified celluloses, such as hydroxypropylated guar gum, methyl hydroxyethyl cellulose, hydroxypropyl methyl cellulose or hydroxyethyl cellulose.

Gelling agents which are representative are modified clays (bentones), metal salts of fatty acids (aluminum stearate), ethylene/acrylate copolymers, silicas, polyethylenes, calcium silicates or ethyl cellulose.

The compositions of the present invention may also contain various ingredients, additives and adjunants conventionally employed in the cosmetic, dermatological or dermopharmaceutical arts, such as colorants and pigments other than titanium dioxides, solvents (water, alcohols, etc.), preservatives, perfumes, hydrating agents, agents absorbing ultraviolet rays (sunscreens, inorganic pigments other than titanium dioxides), pulverulent agents other than the deformable hollow particles, bactericidal agents and/or odor-absorbers.

Too, the subject compositions may contain one or more hydrophilic and, more preferably, lipophilic, cosmetic or dermatological active agents, especially with a view to treating and/or preventing skin afflictions such as acne, mycosis, eczema, rosacea, seborrhoeic dermatitis, heliodermatitis, skin aging and disease states affecting the scalp. These compositions for skin treatment are topically administered.

The compositions of the invention may be formulated according to techniques which are well known to a this art, in particular those intended for the preparation of emulsions of oil-in-water or water-in-oil type.

The subject compositions may, in particular, be formulated as emulsions, simple or complex (O/W, W/O, O/W/O or W/O/W), in such form as a cream, a milk, a gel, a lotion, an ointment or a cream gel, a powder, or as a solid stick, and may optionally be packaged as an aerosol and may be provided in the form of a foam or spray.

This invention is particularly well suited for the formulation of compositions of the anhydrous type, especially anhydrous creams.

In order to further illustrate the present invention and the advantages thereof, the following specific examples are given, it being understood that same are intended only as illustrative and in nowise limitative.

In said examples to follow, comparative tests were carried out to evidence the improvement attained in respect of the photobluing and whitening on skin by incorporating deformable hollow microspheres of an expanded copolymer of vinylidene chloride and acrylonitrile, or vinylidene chloride, acrylonitrile and methacrylate, into compositions containing titanium dioxide pigments.

EXAMPLE 1

An anhydrous composition was formulated, containing a certain percentage x of Expancel and 20% of titanium dioxide, in an anhydrous vehicle comprising a polyalkoxylated fatty alcohol (oxypropylenated butyl alcohol), a fatty substance from the ester family (isopropyl palmitate), a wax whose melting point ranged from 60° to 80° C. (hydrogenated castor oil), a thickening fatty substance (glycerol monostearate) and an oil (hydrogenated polydecene).

Five different compositions A, B, C, D and E were thus prepared, with the content x varying from 0% to 2%.

For these five compositions, the photobluing was evaluated according to the following procedure: the compositions were introduced into plastic boxes which were transparent to UV (50×40×6 cm$^3$ crystaline polystyrene boxes) and exposed to UV irradiation (Heraeus Suntest CPS) for 1 hour. Colorimetric measurements were performed using a Minolta CM1000 colorimeter; a first measurement was taken just before the exposure to the UV irradiation ($T_0$) and a second after one hour of exposure to the UV irradiation ($T_1H$).

The results are expressed in the (L, a, b) system, in which L represents the luminance, a represents the red-green axis (−a=green, +a=red) and b represents the yellow-blue axis (−b=blue, +b=yellow).

To evaluate the photobluing, the values of interest are $\Delta b$, which measures the change in the blue coloration, $\Delta L$, which measures the blackening of the composition, and $\Delta E$, which measures the total color change. More precisely, $\Delta b$ and $\Delta L$ are defined by $\Delta b = b_{T_1H} - b_{T_0}$ and $\Delta L = L_{T_1H} - L_{T_0}$. The lower the $\Delta b$, the more effective is the protection against photobluing.

$\Delta E$ is calculated from the variations $\Delta L$, $\Delta a$ and $\Delta b$ according to the following formula:

$$\Delta E = \sqrt{(\Delta L)^2 + (\Delta a)^2 + (\Delta b)^2}$$

The results obtained are reported in the following Table (I):

TABLE (I)

| Formula | x % | ΔL | Δb | ΔE |
|---|---|---|---|---|
| A (comparative) | 0 | 10.7 | 7.7 | 13.60 |
| B | 0.2 | 8.0 | 4.45 | 9.55 |
| C | 0.5 | 3.15 | 0.27 | 3.30 |
| D | 1 | 4.6 | 0.95 | 4.80 |
| E | 2 | 2.75 | 0.14 | 2.80 |

These results clearly evidence that the incorporation of deformable hollow microspheres of an expanded copolymer of vinylidene chloride and acrylonitrile, or vinylidene chloride, acrylonitrile and methacrylate, into an anhydrous composition comprising a titanium dioxide significantly decreased the photobluing due to the presence of said titanium dioxide.

EXAMPLE 2

The five anhydrous compositions A, B, C, D and E of Example 1 were again tested and the whitening observed when these compositions were applied onto skin was evaluated.

For this evaluation of whitening, tests were carried out on five models. The intensity of the whitening (Iw) was measured on a scale graduated from 0 to 5. The value 0 corresponds to a very whitening composition, whereas the value 5 corresponds to a composition that whitens only very slightly.

The results obtained are reported in the following Table (II):

TABLE (II)

| Formula | x % | Iw |
|---|---|---|
| A (Comparative) | 0 | 2 |
| B | 0.2 | 2.9 |
| C | 0.5 | 2.8 |
| D | 1 | 3.6 |
| E | 2 | 3.7 |

These results clearly evidence that the incorporation of deformable hollow microspheres of an expanded copolymer of vinylidene chloride and acrylonitrile, or of vinylidene chloride, acrylonitrile and methacrylate, into a composition comprising a titanium dioxide significantly decreased the whitening of the composition when it was applied onto skin.

EXAMPLE 3

Three oil-in-water (O/W) emulsions containing a certain percentage x of Expancel and 20% of titanium oxide and with the following formulation were prepared (the amounts are given in % by weight relative to the total weight of the composition):

Phase A:
  (i) expanded microspheres of vinylidene chloride/ acrylonitrile/methyl methacrylate copolymer, containing isobutane, marketed under the trademark "Expancel 551 DE" by Nobel Casto x %

(ii) cetylstearyl alcohol oxyethylenated with 12 EO, marketed under the trademark "Eumulgin B1" by Henkel (emulsifier) 3.3%

(iii) glycerol monostearate marketed under the trademark "Tegin 90" by Goldschmidt (emulsifier) 1.7%

(iv) dicaprylyl ether marketed under the trademark "Cetiol OE" by Henkel (oil) 17.5%

(v) cyclohexadimethylsiloxane marketed under the trademark "Dow Corning 246 Fluid" by Dow Corning (oil) 5.6%

Phase B:

(vi) titanium dioxide marketed under the trademark "MT 100T" by Tayca (pigment) 20%

Phase C:

(vii) hydroxyethyl cellulose marketed under the trademark "Natrosol 250 HHR" by Aqualon (thickener) 0.5%

(viii) xanthan gum marketed under the trademark "Keltrol T" by Kelco (thickener) 0.4%

Phase D (ix) hydrating agents 15%

(x) preservatives q.s.

Phase E:

(xi) purified water q.s. 100%

The emulsions were prepared as follows: Phase A was heated to 90° C. Half the phase E and the phase D, both preheated to 90° C., were then added thereto and mixed with stirring to produce the emulsion. Phase B was added with stirring and then phase C, dispersed beforehand in the other half of Phase E. Cooling was continued to ambient temperature.

Three different OW emulsions 1, 2 and 3 were thus prepared, the content x varying from 0% to 1%.

Three water-in-oil (W/O) emulsions containing a certain percentage x of Expancel and 20% of titanium dioxide, and of the following formulation were also prepared (the amounts are given in % by weight relative to the total weight of the composition):

Phase A1:

(i) expanded microspheres of vinylidene chloride/acrylonitrile/methyl methacrylate copolymer containing isobutane, marketed under the trademark "Expancel 551 DE" by Nobel Casto x %

(ii) oxyethylenated polydimethyl/methyl cetyl/methylsiloxane marketed under the trademark "Abil EM 90 D" by Goldschmidt (emulsifier) 2%

(iii) isoarachidyl neopentanoate marketed under the trademark "Elefac 1205" by Bernel (oil) 10%

(iv) 2,2,4,4,6,6,8-heptamethylnonane marketed under the trademark "Isohexadecane" by Bayer (oil) 10%

(v) natural beeswax marketed by Barlocher 1.5%

(vi) "Cero 20 EG 626" marketed by Barlocher (wax/thickener) 1%

Phase A2:

(vii) titanium dioxide marketed under the trademark "MT 100T" by Tayca (pigment) 20%

Phase B:

(viii) sodium chloride 2%

(ix) magnesium sulfate 0.7%

(x) hydrating agents 12%

Phase C:

(xi) purified water q.s. 100%

These emulsions were prepared as follows: phase A1 was heated to 80° C. and then phase A2 was added with stirring.

Phase C and B were then heated to 80° C. Phase A1, A2, C and B were then mixed with stirring and the cooling was continued to ambient temperature.

Three different W/O emulsions 4, 5 and 6 were thus prepared, the content x varying from 0% to 1%.

The procedure for evaluating the photobluing was the same as in Example 1.

The results obtained are reported in the following Table (III), wherein Δb, ΔL and ΔE are as defined in Example 1:

TABLE (III)

| Emulsion | x % | ΔL | Δb | ΔE |
|---|---|---|---|---|
| 1 (O/W) comparative | 0 | 24.05 | 16.55 | 29.70 |
| 2 (O/W) invention | 0.5 | 15.50 | 9.65 | 18.75 |
| 3 (O/W) invention | 1 | 12.85 | 8.85 | 16.10 |
| 4 (W/O) comparative | 1 | 22.80 | 18.00 | 29.65 |
| 5 (W/O) invention | 0.5 | 18.30 | 13.65 | 23.45 |
| 6 (W/O) invention | 1 | 16.60 | 12.65 | 21.55 |

These results clearly evidence that the introduction of deformable hollow microspheres of an expanded copolymer of vinylidene chloride and acrylonitrile, or of vinylidene chloride, acrylonitrile and methacrylate, into an O/W or W/O emulsion containing a titanium dioxide significantly decreased the photobluing due to the presence of said titanium dioxide.

EXAMPLE 4

The following composition is a specific example of a high-protection anhydrous sun cream in accordance with the invention. The amounts are expressed in % by weight relative to the total weight of the composition:

Phase A:

(i) butyl alcohol oxypropylenated with 14 PO, marketed under the trademark "Ucon Fluid AP" by Amerchol (emulsifier) 12%

(ii) isopropyl palmitate marketed under the trademark "Estol 1517" by Unichema 12%

(iii) hydrogenated castor oil marketed under the trademark "Cutina HR" by Henkel 7.5%

(iv) glycerol monostearate marketed under the trademark "Tegin 90" by Goldschmidt 0.25%

Phase B:

(v) titanium oxide marketed under the trademark "MT 100T" by Tayca 20%

(vi) magnesium silicate marketed under the trademark "Talc Luzenac 15 M00" by Luzenac 5%

(vii) expanded microspheres of vinylidene chloride/acrylonitrile/methyl methacrylate copolymer containing isobutane, marketed under the trademark "Expancel 551 DE" by Nobel Casto 0.5%

(viii) hydrogenated polydecene (MW 549) marketed under the trademark "Silkflo S 366 NF" by Albemarle q.s. 100%

This cream was formulated as follows: phase A was heated to 90° C. to homogenize same. The pigmented paste was then prepared by mixing the titanium oxide with the hydrogenated polydecene. Talc was added to this mixture, followed by the Expancel. Phase B thus prepared was heated to 90° C. The two phases A and B were then mixed using a Rayneri mixer. Once the mixture set solid, it was heated again to 90° C. The mixture was then turbine-blended in a Turrax mixer for 10 minutes. The cream was then permitted to cool to ambient temperature under Rayneri stirring.

This cream was very slightly subject to photobluing and whitened only very slightly when applied to the skin.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for reducing the photobluing effect on skin of a topically applicable cosmetic/sunscreen/dermatological composition comprising at least one titanium dioxide nanopigment, which comprises adding to said composition an effective photobluing reducing amount of deformable, hollow particulates having a particle size ranging from 1 to 250 μm and comprising an expanded copolymer of vinylidene chloride, acrylonitrile and a (meth)acrylate.

2. The method of claim 1, said deformable hollow particulate having a particle size of less than 100μ.

3. The method of claim 1, wherein said topically applicable cosmetic/sunscreen/dermatological composition comprises deformable hollow particulates having a particle size ranging from 10μ to 60μ.

4. The method as defined by claim 1, wherein said topically applicable cosmetic/sunscreen/dermatological composition comprises deformable hollow particulates having a density ranging from 15 kg/m³ to 200 kg/m³.

5. The method as defined by claim 4, wherein said topically applicable cosmetic/sunscreen/dermatological composition comprises hollow particulates having a density ranging from 40 kg/m³ to 100 kg/m³.

6. The method as defined by claim 1, wherein said topically applicable cosmetic/sunscreen/dermatological composition comprises from 0.1% to 10% by weight of said deformable hollow particulates.

7. The method as defined by claim 1, wherein said topically applicable cosmetic/sunscreen/dermatological composition comprises from 0.3% to 5% by weight of said deformable hollow particulates.

8. The method as defined by claim 1, wherein said topically applicable cosmetic/sunscreen/dermatological composition comprises at least 5% by weight of said at least one titanium dioxide nanopigment.

9. The method as defined by claim 8, wherein said topically applicable cosmetic/sunscreen/dermatological composition comprises at least 10% by weight of said at least one titanium dioxide nanopigment.

10. The method as defined by claim 9, wherein said topically applicable cosmetic/sunscreen/dermatological composition comprises at least 15% by weight of said at least one titanium dioxide nanopigment.

11. The method as defined by claim 1, wherein said cosmetic/sunscreen/dermatological composition comprises at least one titanium dioxide pigment which is treated with a metal or metal compound selected from the group consisting of silica, alumina, an aluminum compound, silicon, sodium, an iron oxide, an iron ester, or stearic acid, or glycerol.

12. The method as defined by claim 1, wherein said topically applicable cosmetic/sunscreen/dermatological composition further comprises at least one other agent selected from the group consisting of a thickener, emulsifying agent, gelling agent, hydrophilic active substance, lipophilic active substance, perfume, preservative, solvent, and a colorant.

13. The method as defined by claim 1, wherein said topically applicable cosmetic/sunscreen/dermatological composition is in a form selected from the group consisting of an oil-in-water emulsion, a water-in-oil emulsion, a cream, a lotion, a gel, a balm, a milk, a blusher, a fluid or cast foundation, a foam, a spray, and a dermopharmaceutical ointment.

14. The method as claim 1, wherein said topically applicable cosmetic/sunscreen/dermatological composition is in the form of a makeup.

15. The method as defined by claim 1, wherein said topically applicable cosmetic/sunscreen/dermatological composition further comprises at least one oil or wax.

16. The method as defined by claim 1, wherein said topically applicable cosmetic/sunscreen/dermatological composition further comprises a cosmetically or pharmaceutically acceptable vehicle, diluent or carrier.

* * * * *